United States Patent [19]

Sato et al.

[11] Patent Number: 5,418,826
[45] Date of Patent: May 23, 1995

[54] FLUORESCENT X-RAY QUALITATIVE ANALYTICAL METHOD

[75] Inventors: Yoshimichi Sato; Akimichi Kira, both of Miyanohigashi, Japan

[73] Assignee: Horiba, Ltd., Kyoto, Japan

[21] Appl. No.: 134,336

[22] Filed: Oct. 12, 1993

[30] Foreign Application Priority Data

Oct. 11, 1992 [JP] Japan .................. 4-299290
Oct. 11, 1992 [JP] Japan .................. 4-299291
Oct. 17, 1992 [JP] Japan .................. 4-304784

[51] Int. Cl.⁶ .......................... G01N 23/223
[52] U.S. Cl. .......................... 378/48; 378/45
[58] Field of Search .......... 378/44, 45, 46, 48, 378/49, 50

[56] References Cited

U.S. PATENT DOCUMENTS 4,429,409 1/1984 Berry et al. ............... 378/48 X
4,510,573 4/1985 Boyce et al. ............... 378/48 X
5,062,127 10/1991 Sayama et al. ............. 378/48 X Primary Examiner—David P. Porta
Attorney, Agent, or Firm—Price, Gess & Ubell

[57] ABSTRACT

The present invention provides a fluorescent X-ray qualitative analytical method of determining elements in a sample by preliminarily measuring a standard peak position corresponding to an energy position of fluorescent rays generated from each element expected in a sample. The standard peak positions are then stored. The sample is then radiated with X-rays to cause fluorescent X-rays to be generated from the elements in the sample. Spectral data is obtained from the fluorescent X-rays to determine the peak-generating positions from the spectral data and then a comparison is made with the stored standard peak positions to determine the elements contained in the sample.

15 Claims, 11 Drawing Sheets

Fig. 8

The initial intensity of the peak A $N_A^0$ = ROI intensity of $E_1$ to $E_2$

The initial intensity of the peak B $N_B^0$ = ROI intensity of $E_3$ to $E_4$

— 201

202

The overlap factor is obtained from the peak function of the fluorescent X-rays A $f_A(x_i)$ and the peak function of the fluorescent X-rays B $f_B(x_i)$ $$H_{AB} = \sum_{x=E_3}^{E_4} f_A(x) \Big/ \sum f_A(x)$$

$$H_{BA} = \sum_{x=E_1}^{E_2} f_B(x) \Big/ \sum f_B(x)$$

wherein $f_A(x_i)$ and $f_B(x_i)$ are the functions previously known for every apparatus.

(Followed by the step 203 in Fig. 9)

FLUORESCENT X-RAY QUALITATIVE ANALYTICAL METHOD

BACKGROUND OF THE INVENTION

1. Field of the Invention

The present invention relates to a fluorescent X-ray qualitative analytical method and in particular to a fluorescent X-ray qualitative analytical method capable of accurately analyzing a sample containing a number of elements generating a plurality of fluorescent X-rays having adjacent energies, such as Mo (molybdenum)-$\alpha$ and S (sulfur)-K$\alpha$, Mo-K$\alpha$, and Mo-K$\alpha_2$ or Rh-K $\alpha_1$, and Rh-K$\alpha_2$, respectively.

2. Description of Related Art

In a fluorescent X-ray analyzer, as shown in FIG. 17, X-rays are incident upon a sample 2 to be measured from an X-ray generator 1 and fluorescent X-rays 3 emitted from the sample 2 are detected by means of a detector 4. Spectral data, as shown in FIG. 18, is obtained by means of a data-collecting device 41.

Since an energy value of fluorescent X-rays 3 emitted from the sample are fixed for every element contained in the sample 2, the spectral data will show peaks at energy positions corresponding to the elements contained in the sample 2. It is possible to specify the elements contained in the sample 2 from the specific positions of the peaks.

In a conventional qualitative analytical procedure, the spectral data can have a reliability from a high probability to a low probability, depending on the existence of peaks at energy positions of the fluorescent X-rays relative to the respective elements being examined. If a definite peak exists at an energy position of the fluorescent X-rays obtained from a certain element, it will be judged that the element is contained in the sample 2, while, if the peak does not exist, it is judged that the element is not contained.

However, in the case where a plurality of elements in the sample 2 may generate fluorescent X-rays having adjacent energies, such as Mo-L$\alpha$ and S-K$\alpha$, then even though it is intended to measure spectra 5 and 6 of an element showing a peak profile of fluorescent X-rays A and an element showing a peak profile of fluorescent X-rays B having peaks 8 and 9 at energy positions corresponding to these elements, as shown in FIG. 7, the peak-generating positions of the spectra 5, 6 are not detected at the peak positions 8, 9, but are rather detected as a combined peak position 10 of a measured spectrum 7 because of the resolution of the detector 4. Accordingly, even though an element showing the peak profile of fluorescent X-rays A and an element showing the peak profile of fluorescent X-rays B exist in the sample 2, the spectra 5,6 cannot be measured from the obtained spectral data so that a mistaken qualitative analytical result will occur. If a permissible range of coincidence of the peak positions is extended in order to avoid the above described disadvantages, the peak positions 8, 9 still remain adjacent to each other even in the case where merely the energy spectrum 5 exists, so that there is still a possibility that an existence of the spectrum 6 is judged.

In addition, there is also the possibility that a spectrum 25 high in importance and having a peak position (a) generated from a certain element is overlapped by another spectrum 26 having a peak position (b) and thus the spectrum 25 cannot be recognized as an independent element having the peak position (a), as shown in FIG. 19, in the spectral data obtained from the sample 2. This can lead to a misjudgment that certain elements are not contained in the sample and thus it is difficult to accurately conduct a qualitative analysis.

SUMMARY OF THE INVENTION

The present invention has been achieved in view of the above described problems and it is an object of the present invention to provide a fluorescent X-ray qualitative analytical method capable of accurately measuring elements even from a sample containing elements generating a plurality of fluorescent X-rays having adjacent energies.

A fluorescent X-ray qualitative analytical method according to the present invention comprises preliminarily measuring a standard peak position of a peak corresponding to an energy position of fluorescent rays generated from each element when applied with X-rays for every element or determining a standard peak position of each element by a calculation. Obtaining spectral data from the fluorescent X-rays generated from a sample to be measured to determine a peak-generating position from the spectral data, and providing a comparative operation, in which the peak-generating position obtained from the spectral data is compared with the standard peak position of each element preliminarily determined in order to judge whether an element is contained in the sample if the peak-generating position of the spectral data from the sample to be measured coincides with the standard peak position of each element. X-rays are generated from an X-ray generator and incident upon the sample to be measured so that the fluorescent X-rays emitted from the sample are detected by means of a detector, and signals are read as the spectral data through a signal operating means.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 8 is a flow chart showing the first half of an overlapped factor method in the second preferred embodiment;

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide fluorescent X-ray qualitative analytical method.

Figure 2:
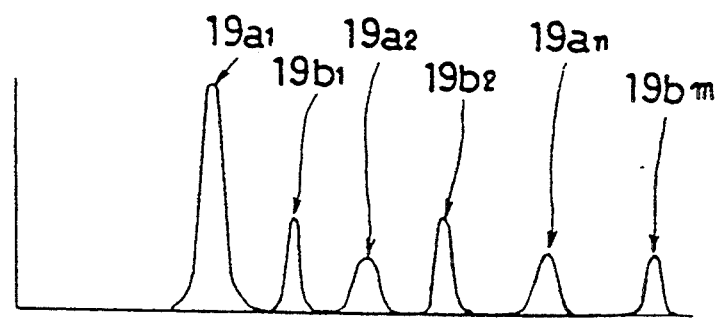
FIG. 2 is a drawing showing a spectrum obtained in one step in a first preferred embodiment of the present invention.
Figure 3:
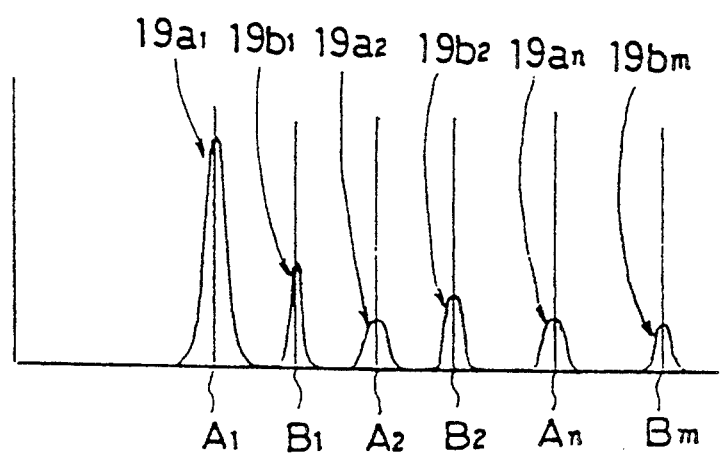
FIG. 3 is a drawing showing standard peak positions of the spectrum obtained in the preferred embodiment.

In practicing the present invention, preliminary measurements are taken to determine the standard peak positions of the elements desired to be identified in the operation of the instrument. The standard peak position can be done by an empirical measuring or by a theoretical calculation for each of the individual elements. In essence, the energy value of the fluorescent X-rays that are generated by each element is ascertained so that the peak positions formed at those energy positions corresponding to the respective elements can then be memorized as standard peak positions for each element. As an example of determining a standard peak position, reference can be made to FIG. 2 wherein a sample that is consisting of only one element is radiated with X-rays and then measured to obtain the spectral data $19a_1$, $19a_2$, $19a_n$ within a particular detecting range of the detector. Alternatively, these positions can be calculated by simulation calculation taking into account the resolution of the detector. This procedure is repeated for each of the elements. For example, as shown in FIG. 2, the spectral data $19b_1$, $19b_2$ ... $19b_m$ are obtained in succession to the first data. The area defined by this graph can then be utilized to determine the standard peak positions, as shown in FIG. 3. Thus, peak positions $A_1$, $A_2$, and $A_n$ are determined along with $B_1$, $B_2$, and $B_m$. The standard peak positions can be digitized and entered into a memory of a computer 18, as shown in FIG. 1.

Figure 4:
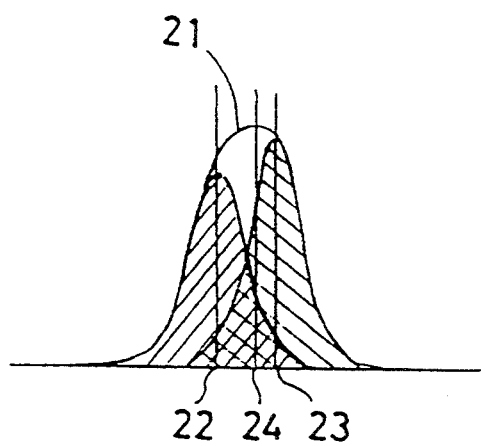
FIG. 4 is a drawing showing standard peak positions of the spectrum obtained in the preferred embodiment.

Referring to FIG. 4, in case of an element generating fluorescent X-rays at adjacent energy positions and thereby providing a pair of closely positioned peak positions 22 and 23, the present invention does not try to determine between this overlapped energy position but rather assumes that this element can be treated as having a spectrum of energy 21, generating one peak at a standard peak position 24. This information is then memorized as the peak position for that type of element.

Figure 1:
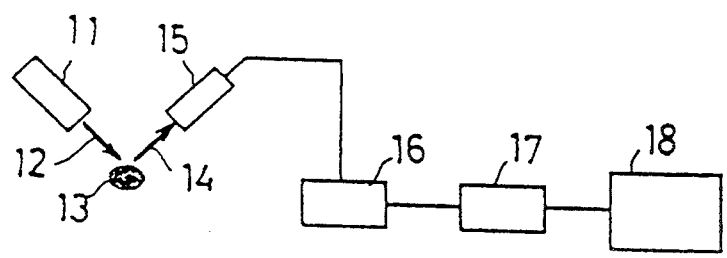
FIG. 1 is a schematic diagram showing one preferred embodiment of an analyzer used in a fluorescent X-ray qualitative analytical method according to the present invention.
Figure 6:
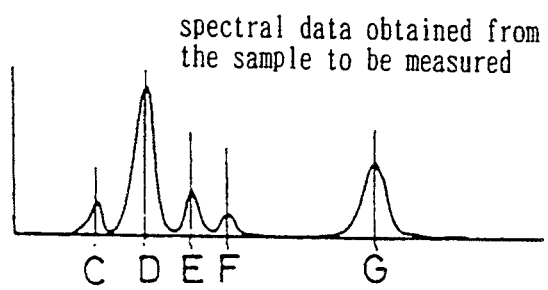
FIG. 6 is a drawing showing peak-generating positions, which are obtained in another step in the preferred embodiment of a sample to be measured.

Referring to FIG. 1, the sample to be measured can then be subject to the primary X-rays to generate the characteristic fluorescent X-rays of the elements contained within the sample. A plot of this information is shown in FIG. 6, and the peak generating positions C through G are calculated from the spectral data, for example, using a multi-channel analyzer 17. These peak-generated positions can then be compared with the stored standard peak positions, which can be retrieved from a computer memory bank. As can be appreciated, there can be an overlaid screen for matching the graphs or the data can be presented in various other formats, including mathematical coordinates. As a result of the comparison of the measured peak positions and the stored peak positions, a determination is then made to determine which elements are considered to be in the sample. As can be appreciated, even an element generating a plurality of fluorescent X-rays having adjacent energies, which is detected as a single peak due to the resolution of the detector, can still be accurately qualitatively analyzed by merely comparing with the stored values.

As can be appreciated, the stored data can be altered to take into consideration the specific resolution of the particular detector as a compensation factor so that the peak positions corresponding to the resolution of a specific detector can still qualitatively determine, in an accurate manner, the elements contained in a sample.

Figure 7:
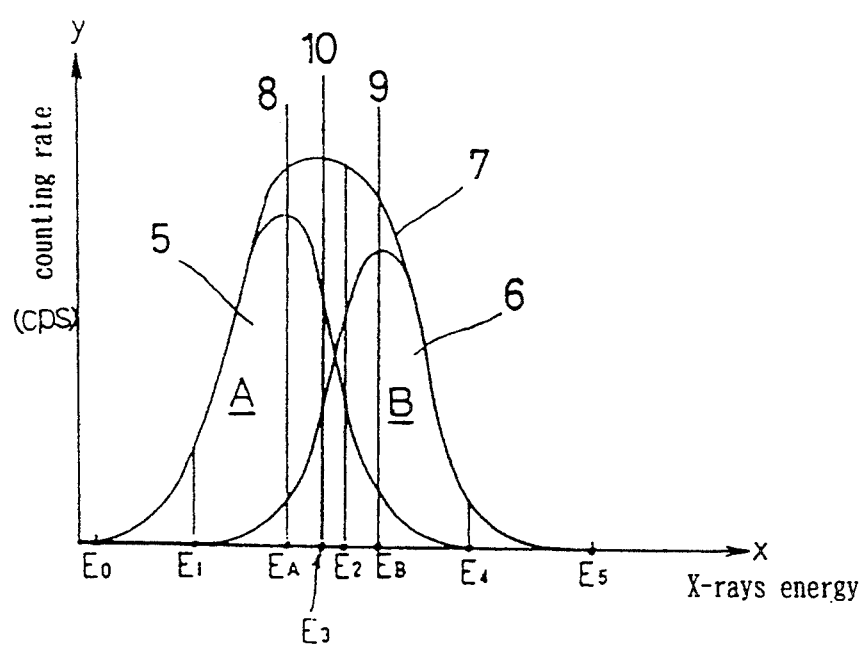
FIG. 7 is a drawing showing an operation of a spectrum which would be detected in a second preferred embodiment of the present invention.
Figure 10:
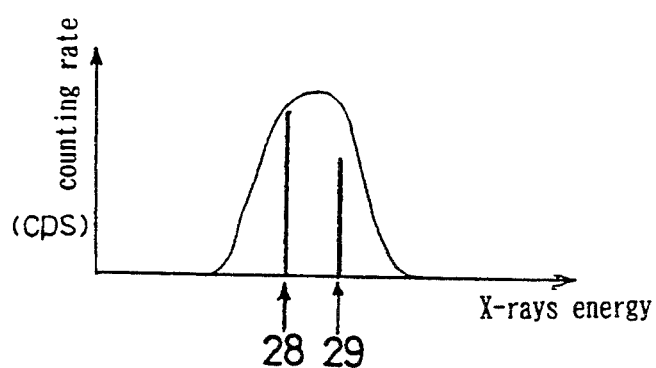
FIG. 10 is a drawing showing a selection of peak positions by a rough qualitative analysis obtained in the second preferred embodiment.

In an alternative embodiment of the present invention, the procedure of comparing to determine the existence of selected elements can be varied and a method of a least square or the overlap factor method can be utilized to make such comparison. For example, the spectral data which is obtained from the fluorescent X-rays emitted from a sample, are used to determine a plurality of peak generating positions from that spectral data. If, for example, a peak generating position 10 is attained, as shown in FIG. 7, then an element having the respective peak-generating positions is primarily selected from a plurality of stored peak-generating positions. In addition, elements having peak-generating positions that can exist in the vicinity of the respective peak-generating positions of the preliminarily selected element are also preliminarily selected. That is to say, elements 28 and 29 having peak-generating positions 8 and 9 will be preliminarily selected on the assumption that the peak-generating positions contained in the peak exist also in the vicinity of the peak-generating position 10 obtained in the initial step, as shown in FIG. 10. One example of this procedure is the method of least square utilizing the following expression 1, set forth below. Referring to FIG. 7, the measured spectrum 7 and the peak profile 5 of fluorescent X-rays A and the peak profile 6 of fluorescent X-rays B are disclosed, respectively.

$$\chi^2 = \sum_{i=1}^{n} [y_i - \{a^* f_A(X_i) + b^* f_B(X_i)\}]^2/(S_i)^2 \quad (1)$$

wherein I is the spectral datum number
$x_i$ is the X-ray energy
$y_i$ is the counting rate (count/sec)
$(S_i)^2$ is the sample dispersion
$f_A(i)$ is the peak function of the fluorescent X-rays A
$f_B(x_i)$ is the peak function of the fluorescent X-rays B
a, b are the coefficients to be determined.

In this preferred embodiment, the coefficients a, b for minimizing $X^2$ in the above described expression (1) are determined.

In addition, the measured intensity of the fluorescent X-rays A is expressed by $$N_A = \sum_{i=1}^{n} {}^* f_A(x_i)$$

while the measured intensity of the fluorescent X-rays B is expressed by $$N_B = \sum_{i=1}^{n} {}^* f_B(x_i)$$

In addition, another example of the spectral operation of the selected elements, in which the overlapped factor method is utilized, will be described below.

Referring to FIG. 8, at first an initial intensity $N_A^0$ of the peak profile of the fluorescent X-rays A is determined in a step 201.

$N_A^0$ = ROl intensity of $E_1$ to $E_2$

Here, ROl is an abbreviation of Region of Interest and means a region where the intensity is to be determined.

Successively, an initial intensity $N_B^0$ of the peak profile of the fluorescent X-rays B is similarly determined.

$N_B^0$ = ROl intensity of $E_3$ to $E_4$

Subsequently, overlap factors $H_{AB}$ are defined as follows in an overlap region of the peak profile of the fluorescent X-rays A and the peak profile of the fluorescent X-rays B are determined from the peak function $f_A(X_i)$ of the fluorescent X-rays A and the peak function $f_B(x_i)$ of the fluorescent X-rays B in a step 202.

$H_{AB} = \Sigma f_A(x) \langle\langle$ wherein $x = E_3$ to $E_4$ in total $\rangle\rangle \div$ $\Sigma f_A(x) \langle\langle$ wherein $x = E_1$ to $E_2$ in total $\rangle\rangle$ $H_{BA} = \Sigma f_B(x) \langle\langle$ wherein $x = E_1$ to $E_2$ in total $\rangle\rangle \div$ $\Sigma f_B(x) \langle\langle$ wherein $x = E_3$ to $E_4$ in total $\rangle\rangle$ However, $f_A(x)$ and $f_B(x)$ are functions previously known depending upon the particular apparatus used in the measurements.

Figure 9:
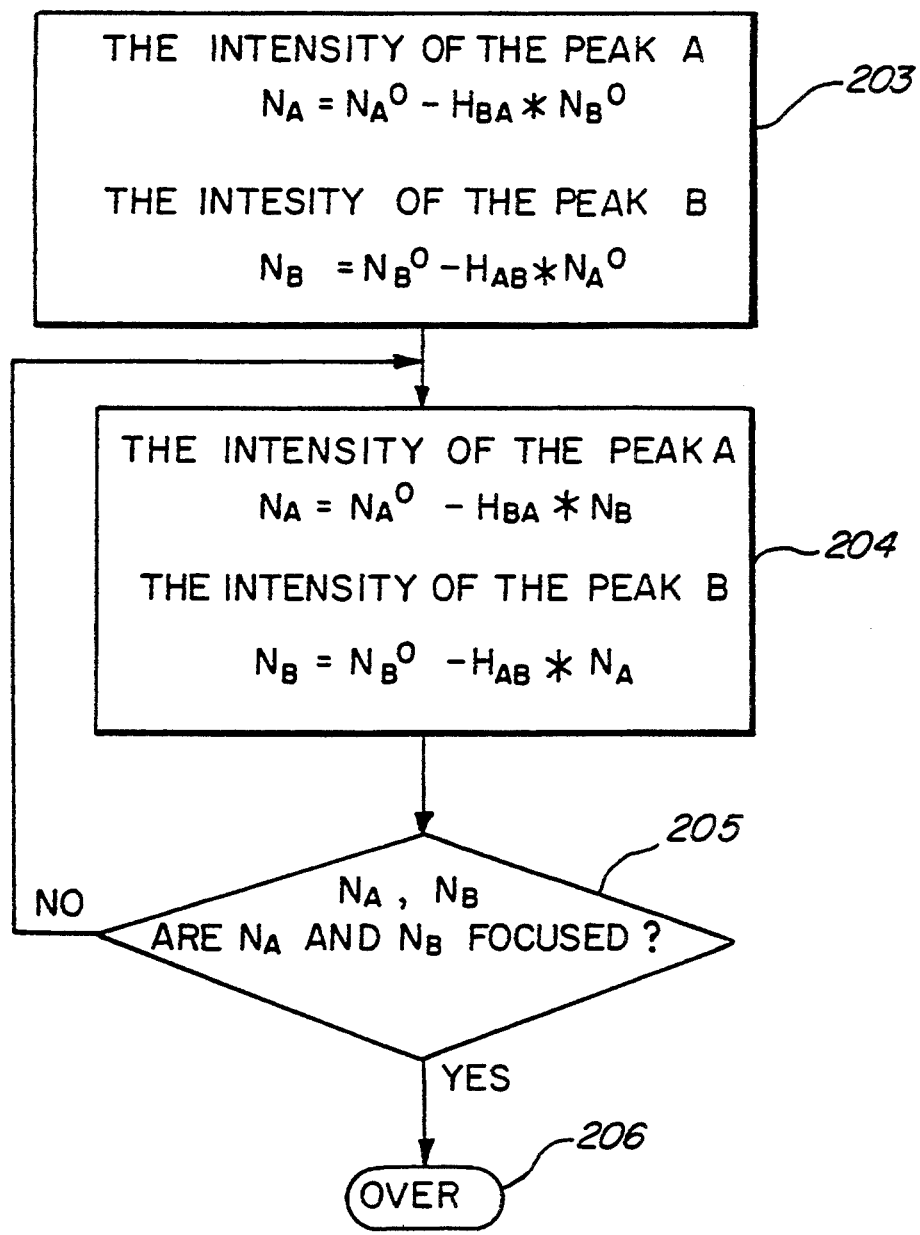
FIG. 9 is a flow chart showing a second half of an overlapped factor method in the second preferred embodiment.

Subsequently, a measured intensity relating to the ROl intensity of the fluorescent X-rays A is determined by the following expression in a step 203 in FIG. 9.

$$N_A = N_a^0 - H_{BA}{}^* N_B^0$$

A measured intensity relating to the ROl intensity of the fluorescent X-rays B is similarly determined by the following expression:

$$N_B = N_B^0 - H_{AB}{}^* N_A^0$$

Subsequently, a measured intensity of the fluorescent X-rays A is determined by the following expression in a step 204, $$N_A = N_A^0 - H_{BA}{}^* N_B$$

A measured intensity of the fluorescent X-rays B is similarly determined by the following expression:

$$N_B = N_B^0 - H_{AB}{}^* N_A$$

Successively, the respective focused conditions of the measured intensity $N_A$ of the fluorescent X-rays A and the measured intensity $N_B$ of the fluorescent X-rays B are analyzed on the basis of this data in a step 205.

If it is judged that both the measured intensity $N_A$ and the measured intensity $N_B$ are focused, then the peak separation in step 206 is over.

Thus, the measured intensity $N_A$ of the fluorescent X-rays A and the measured intensity $N_B$ of the fluorescent X-rays B can be obtained through the above described steps. If the values of these measured intensities $N_A$, $N_B$ are of a certain value or more, it is judged that the element generating the fluorescent X-rays A and the fluorescent X-rays B is contained in the sample to be measured.

Figure 11:
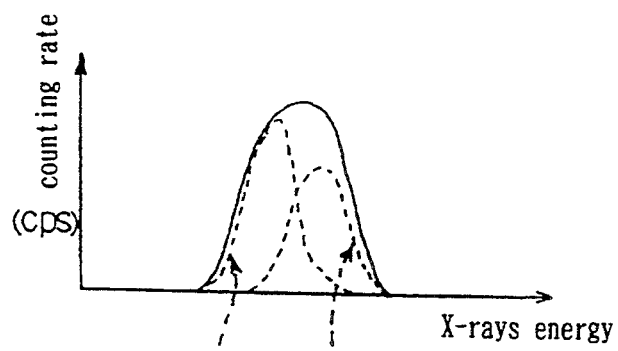
FIG. 11 is a drawing showing a peak-separation by a spectral operation obtained in the second preferred embodiment.

As a result, as shown by dotted lines expressing the spectra 31, 32 in, for example, FIG. 11, the element showing the peak profile of the fluorescent X-rays A and the element showing the peak profile of the fluorescent X-rays B are measured not to bring about a conventional erroneous qualitative analytical result that these elements are not contained because no peak was measured at the peak positions 8, 9 and thus an accurate qualitative analysis can be achieved. In addition, in the case where merely the peak profile of the fluorescent X-rays A was measured, a mistaken qualitative analytical result that an element showing the peak profile of the fluorescent X-rays B is not contained in the sample is not brought about.

The present invention provides a fluorescent qualitative analytical method comprising a step of obtaining spectral data from fluorescent X-rays emitted from a sample to determine peak-generating positions generated in the spectral data; a step of comparing the peak generating positions obtained from the spectral data with preliminarily fixed standard peak positions of the respective elements to digitalize a coincident degree of the peak-generating positions with the standard peak positions, and a step of judging that an element is contained in the sample to be measured in the case where the obtained value is a certain value or more while it is judged that the element is not contained in the sample in the case where the obtained value is less than the certain value.

Figure 19:
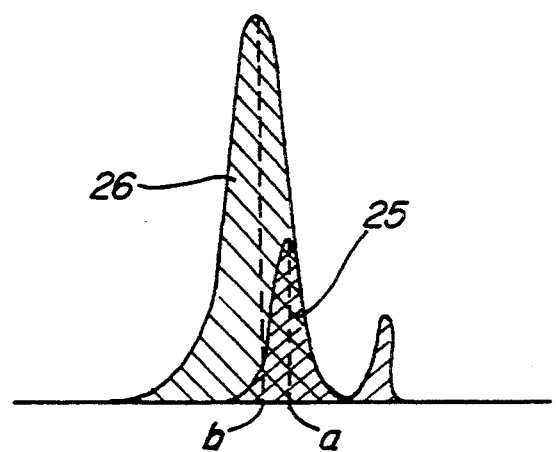
FIG. 19 is a drawing showing an analytical method in the conventional example.

The conventional disadvantage of this judging a spectrum 25 having relatively high importance because a peak position A generated from a certain element is overlapped on another spectrum 26 having peak position B, as shown in FIG. 19, can be avoided. In addition, the present invention further facilitates the comparison step to determine a coincident degree of the peak-generating positions with the standard peak positions by digitizing the measured data. This digitalization can be conducted by the following expression (2).

$$y = \Sigma\{[(A \times h - \Delta E) \times I]/(A \times h)\}/\Sigma I \quad (2)$$

wherein when $A \times h - \Delta < 0$ holds good, $A \times h - \Delta E$ is defined as 0.

y is the value for a certain element

A is the coefficient h is the height of the peak measured $\Delta E$ is the shift between the peak-generating position (peak position measured) and the standard peak position (peak position) generated from the certain element.

I is the weight corresponding to the generating probability of the peak.

Thus, by digitizing and by providing a weighting factor correspond to the generating probability of a peak, a comparison can be made for determining the elements that are found in the sample data. As can be readily determined, the value of the judging standard can be made variable for every element, or the value of the judging standard can be made variable in correspondence to the sample system to measure.

As mentioned above, the standard peak position of the respective elements can be computed either empirical or calculated and are then stored for comparison with the peak-generating positions obtained from the spectral data from the sample. It is usually preferable that the values of the existing data table are memorized in a computer 18, for example, as shown in FIG. 1. But they also can preliminarily determined by other methods. Because the energy values of the fluorescent X-rays generated from the elements are fixed for every element, the peak positions formed at the energy positions corresponding to the respective elements can accordingly be memorized as the standard peak positions for every element.

Figure 12:
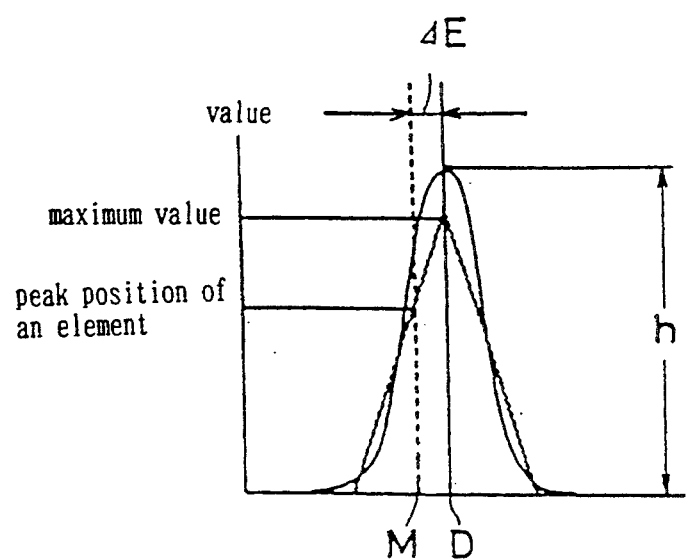
FIG. 12 is a diagram including a step of digitalizing in a third preferred embodiment of the present invention.
Figure 15:
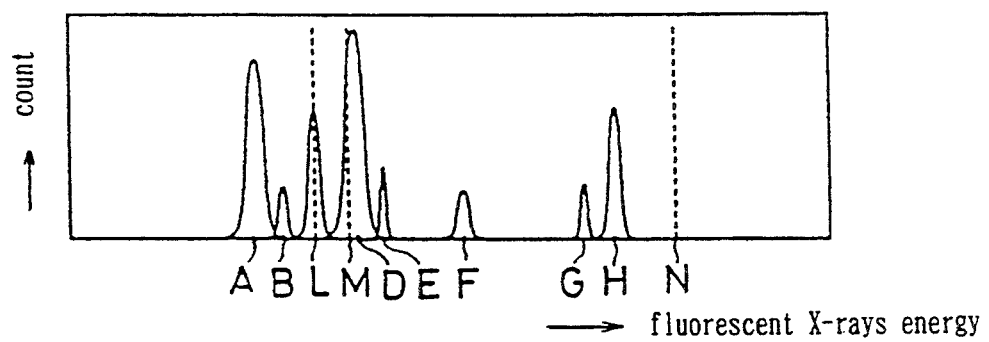
FIG. 15 is a drawing showing spectral data obtained from a sample to be measured containing a plurality of kinds of elements in the third preferred embodiment.

Referring to FIGS. 12 and 15, the standard peak positions L, M, N correspond to the energy positions of the fluorescent X-rays generated from a certain element. These standard peak positions can be determined in turn from a plurality of obtained spectra. These standard peak positions L, M, and N are memorized in the computer 18. The spectral data obtained from fluorescent X-rays 12 emitted from a sample 13 can be utilized to determine the peak-generating positions depicted in that spectral data, as shown in FIG. 1. The spectral data obtained from the sample is shown in FIG. 15 and the peak-generating positions A through H are depicted by signal operating means, including a multi-channel analyzer 17 shown in, for example, FIG. 1. Subsequently, the peak-generating positions obtained from the spectral data are compared with the preliminarily fixed standard peak positions of the respective elements to digitize the coincident degree of the peak-generating positions with the standard peak positions. A maximum value is given to the coincident degree, if a peak exists at a position coincident with the energy positions of the fluorescent X-rays generated from the element compared and a value is given to the coincident degree in correspondence to a shift degree.

$\Delta E$ and a peak height (h) (refer to FIG. 2), if the peak exists at a position shifted from the energy position of the fluorescent X-rays generated from the element compared, as shown in FIGS. 12 to 15. This value is calculated so as to be reduced with an increased shift of the peak position.

Figure 13:
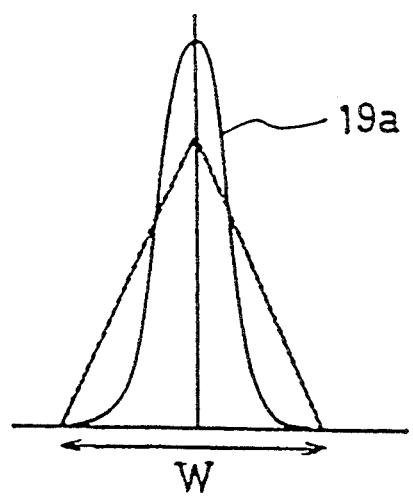
FIG. 13 is a diagram similarly including the step of digitalizing in the third preferred embodiment.
Figure 14:
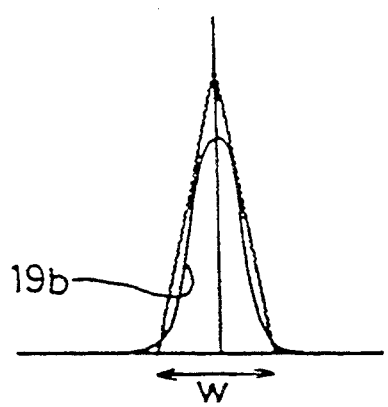
FIG. 14 is a diagram similarly including the step of digitalizing in the third preferred embodiment.

Referring to FIG. 12, when a peak-generating position D is compared with a preliminarily fixed standard peak position M of a certain element compared to determine the value, the shift $\Delta E$ from the peak-generating position (peak position measured) D to the standard peak position (peak position) M generated from the certain element used in comparison, the shift $\Delta E$ of the standard peak position (peak position) from the peak-generating position (peak position measured), is digitalized, but, in FIG. 2, the value is digitalized by 0 in the case where the $\Delta E$ deviated with certain ranges W, w (W > w). Moreover, the wide range W is selected in the case where a peak is generated in spectral data 19a, if the sample 13 is high, as shown in FIG. 13, while a narrow range w is selected in the case where a peak is generated in spectral data 19b from the sample 13 is low, as shown in FIG. 14.

Since fluorescent X-rays having several kinds of energy are generated from one element, this calculation is conducted for energy positions having a possibility of detecting them as the peak generated followed by multiplying by a weight factor (1) corresponding to a probability at which the fluorescent X-rays, having the respective energies, are generated $[A \times h - \Delta) \times I]$. The resulting product is divided by a value of Ah obtained in the case where the energy positions are coincident and the respective values obtained by this calculation are summed up $$\ll \Sigma\{[(A \times h - \Delta E) \times I]/(A \times h)\} \gg .$$

Further, $\Sigma\{[(A \times h - \Delta E) \times I]/A \times h)\}$ is converted into a standardized value y $\ll y = \Sigma\{[(A \times h - \Delta E) \times I]/(A \times h)\}/\Sigma I \ldots (3) \gg$. One example of an expression for such digitalization is given by expression (3).

In summary, the digitalization for the certain element is conducted in correspondence to the shifted degree of the peak and the peak height by the expression (3).

As the result of this digitalization, it is judged that the element is contained in the sample 13 in the case where a value obtained by this method is a certain value or more while it is judged that the element is not contained in the sample 13 in the case where the value obtained is less than the certain value. In the case where it was judged that the element is contained in the sample to be measured 13, the element is added to the qualitative analytical results. Also, in case of the sample containing a plurality of kinds of element, the qualitative analysis can be accurately achieved by conducting this operation for all elements included in the qualitative analytical judgment. In addition, not only a judgment as to whether the element is contained or not is made, but also a judgment of the degree of possibility, at which the element is contained, can be achieved. Moreover, it is possible to make the judging standard variable depending upon the particular sample to be measured.

Since the peak-generating position D, determined when a certain sample 13 was measured, is compared with the preliminarily fixed standard peak positions M of the respective elements and additionally the coincident degree of the peak-generating position D with the standard peak position M is digitalized, the qualitative analysis can be accurately achieved by judging whether a plurality of kinds of elements are contained or not, even in the case of the sample containing them.

Even in the case where the resolution is changed by the exchange of a detector, the resolution is previously known, depending upon that type of detector, so that the coefficient (A) for the digitalization, for example in the above described expression (3), can be set depending upon the resolution of the detector and thus a qualitative analysis can be accurately achieved.

Referring to FIG. 1, reference numeral 11 designates an X-ray generator, reference numeral 13 designating a sample to be measured, reference numeral 15 designating a detector, reference numeral 16 designates an A/D converter, reference numeral 17 designates a multi-channel analyzer, and reference numeral 18 designates a computer.

X-rays 12, emitted from the X-ray generator 11, are incident upon the sample 13. Fluorescent X-rays 14, emitted from the sample 13, are detected by means of the detector 15, and the detected signals are read as spectral data in the computer 18 through an A/D convertor 16 and a multi-channel analyzer 17. The positions of peaks generated from every element are preliminarily memorized in the computer 18.

A method of determining these standard peak positions are shown in FIGS. 2 and 3. Referring to FIGS. 2 and 3, the spectral data are measured for every element or a simulated calculation taking a resolution of the detector into consideration is conducted to obtain data of $19a_1$, $19a_2$, ... $19a_n$; $19b_1$, $19b_2$, ... $19b_m$. The standard peak positions $A_1, A_2, ... A_n$; $B_1, B_2, ... B_m$ of the respective elements are obtained from the data $19a_1$, $19a_2$, ... $19a_n$; $19b_1$, $19b_2$, ... $19b_m$.

On the other hand, in case of an element generating fluorescent X-rays having a plurality of energy values at adjacent positions, it is memorized that one peak is generated at the standard peak position 24 of a spectrum 21. This operation is conducted for all the elements expected to be includes in a qualitative analytical judgment.

Figure 5:
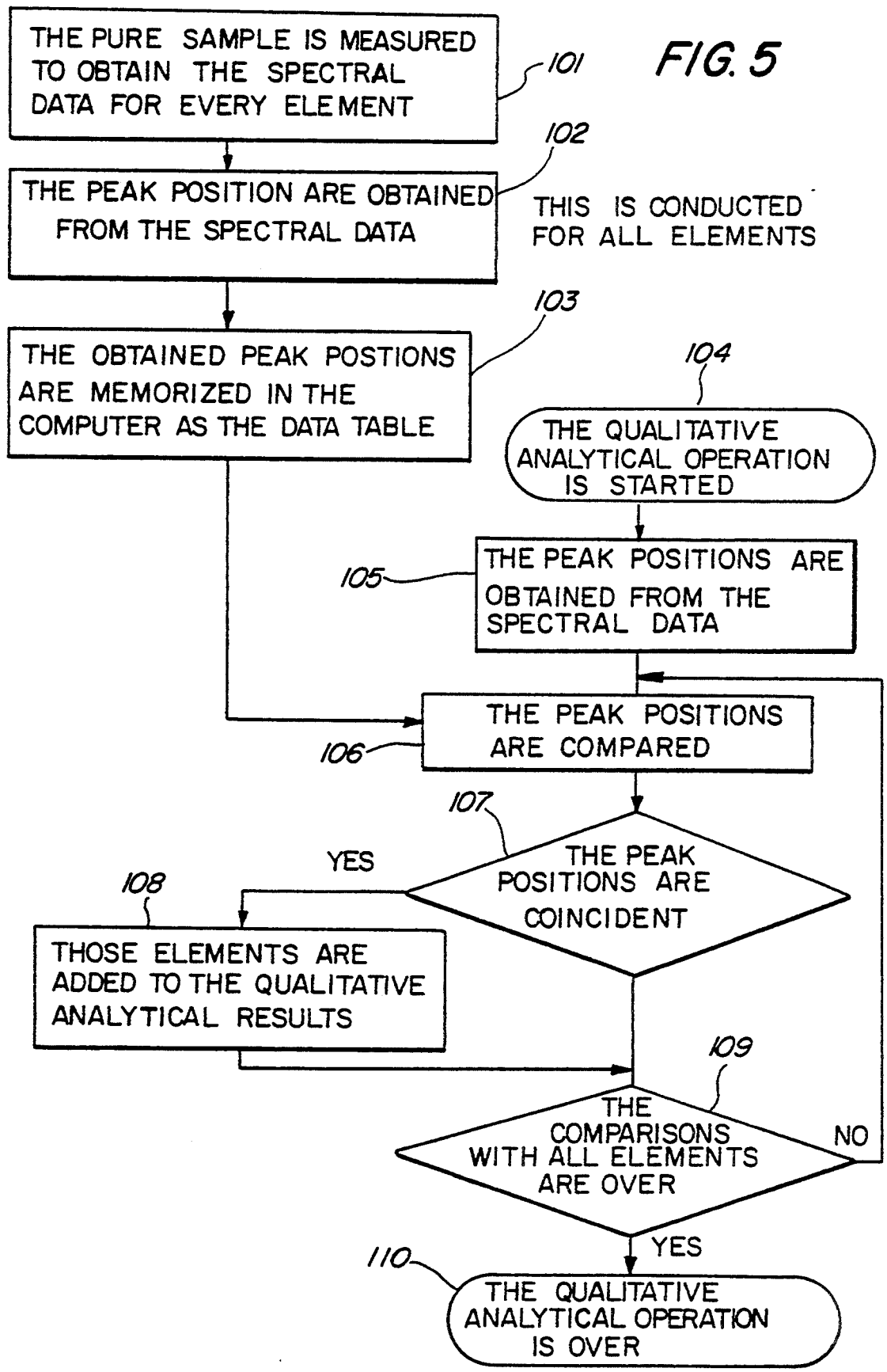
FIG. 5 is a flow chart showing the preferred embodiment.

A procedure of a qualitative analytical operation of the sample is shown in FIG. 5.

Referring to FIG. 5, the qualitative analytical operation is started (refer to a step 104), spectral data shown in FIG. 6 is obtained from the fluorescent X-rays 14, emitted from the sample 13, and peak-generating positions C to G are obtained from the spectral data (refer to a step 105). Successively, the peak-generating positions C to G are compared with the standard peak positions $A_1, A_2, ... A_n$; $B_1, B_2, ... B_m$, which were preliminarily obtained in the order of a step 101, a step 102 and a step 103, of the respective elements (refer to a step 106). As a result of this comparison, if peaks exist at positions, which are the same as the standard peak positions $A_1$, $A_2, ... A_n$; $B_1, B_2, ... B_m$ of the element compared in the spectral data from the sample 13 shown in FIG. 6, it is judged that the element is contained (refer to a step 107 and a step 108). This comparative operation is conducted for all the elements to be qualitatively analyzed (refer to a step 10p9).

By this operation, a qualitative analytical result that an element coincident in peak position (of which peak-generating positions are coincident with the standard peak positions preliminarily memorized for every element) is the element, contained in the sample to be measured 14, is obtained (refer to a step 110).

FIGS. 7 to 11 show a second preferred embodiment of the present invention.

As already shown in FIG. 1, X-rays 12, emitted from an X-ray generator 11, are incident upon a sample to be measured 13, fluorescent X-rays 14, emitted from the sample to be measured 13, are detected by means of a detector 15, and the detected signals are read as spectral data in a computer 18 through an A/D convertor 16 and a multi-channel analyzer 17. Positions of peaks generated from every element are preliminarily memorized in the computer 18.

Spectral data are obtained from fluorescent X-rays, emitted from the sample 13, to determine a plurality of peak-generating positions from the spectral data. For example, a peak-generating position 10 is obtained in FIG. 7. Successively, an element having the respective peak-generating positions is preliminarily selected from a plurality of peak-generating positions and simultaneously also the elements having the peak-generating positions existable in the vicinity of the respective peak-generating positions of the preliminarily selected element, including the respective peak-generating positions, are preliminarily selected for every peak-generating position.

That is to say, elements 28, 29, having peak-generating positions 8, 9, are preliminarily selected on the assumption that the peak-generating positions contained in the peak exist also in the vicinity of the peak-generating position 10, obtained in the above described step (refer to FIG. 10).

A spectral operation of the selected elements is conducted by the use of a method of least square or an overlapped factor method. This method of spectral operation is not limited by these two methods, which have been in general frequently used, but also other methods of spectral operations can be suitably used.

As above described, it has been difficult to judge from merely the peak-generating positions, which element generated the peaks in the case where the peaks in the spectrum are overlapped, but, according to this preferred embodiment, the peaks of the respective elements can be detected by conducting a spectral operation (separation of the peaks) using the method of least square or the overlapped factor method with preliminarily giving the elements included in the peaks as candidates. As a result, the qualitative analysis can be improved in accuracy.

FIGS. 12 to 16 show a third preferred embodiment of the present invention. The positions of peaks LM, N . . . (refer to FIG. 15), generated from every element, are preliminarily memorized in the computer 18.

Figure 16:
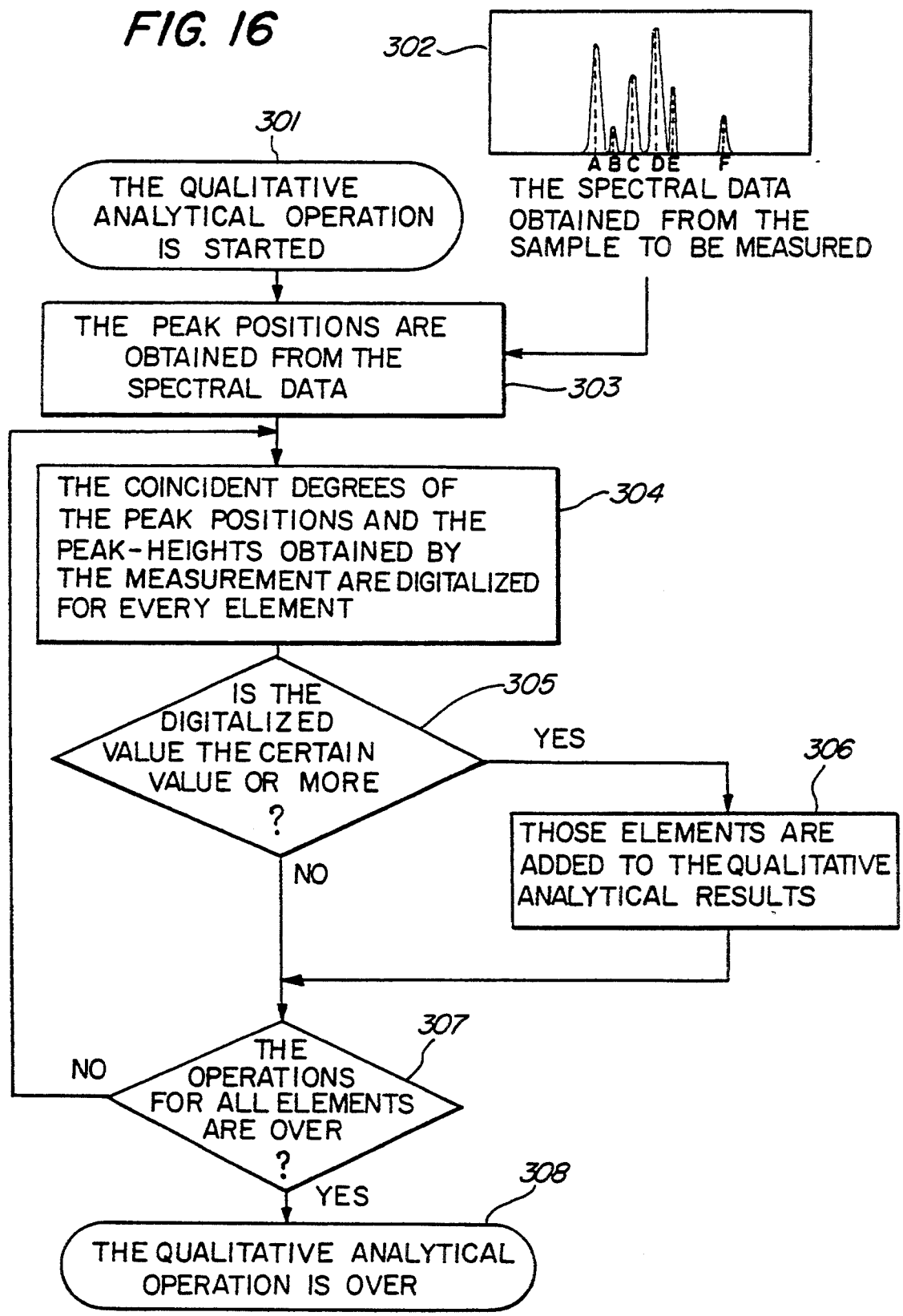
FIG. 16 is a flow chart in the third preferred embodiment.
Figure 17:
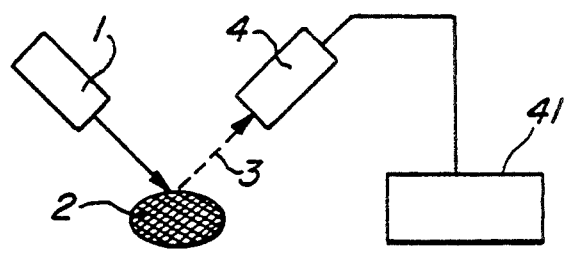
FIG. 17 is a black diagram showing a conventional example.
Figure 18:
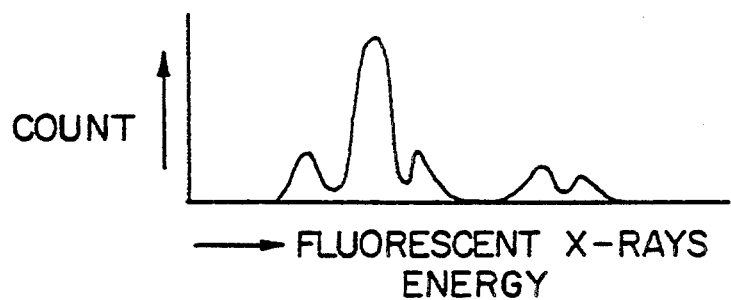
FIG. 18 is a drawing showing a peak-generating position of a sample to be measured in the conventional example.

Referring to FIG. 16, the qualitative analytical operation is started in a step 301, the spectral data being obtained from the fluorescent X-rays 14, emitted from the sample to be measured 13 (refer to a step 302) and peak-generating positions A to F being obtained from the spectral data (refer to a step 303). Successively, the positions of peaks corresponding to energy positions of the fluorescent X-rays generated from the respective elements to be included in a qualitative judgment, are measured for every element to compare the peak-generating positions A to F, G. H with the standard peak positions L, M, N, . . . preliminarily fixed for the respective elements and additionally to coincident degree of the peak-generating positions A to F, G, H with the standard peak positions L, M, N . . . is digitalized by the use of, for example, the above described expression (2) (refer to a step 304).

Subsequently, in the case where the obtained value is a certain value or more, it is judged that the element is contained in the sample 13, while, in the case where the obtained value is less than the certain value, it is judged that the element is not contained in the sample 14 (refer to a step 305), and, in the case where it is judged that the element is contained in the sample to be measured 13, the element is added to the qualitative analytical result (refer to a step 306). This operation is conducted for all elements to be included in the qualitative analytical judgment (refer to a step 307) and thus the qualitative analytical operation is over (refer to a step 308). Even in case of a sample containing a plurality of kinds of element, the qualitative analysis can be accurately achieved. In addition, not only can it be judged whether the element is contained or not, but also a degree of possibility, at which the element is contained, can be obtained. Moreover, the judging standard can be made variable, depending upon the sample system to be measured.

As above described, the fluorescent X-ray qualitative analytical method according to this preferred embodiment, has an advantage in that the qualitative analysis can be accurately achieved by comparing the peak-generating positions obtained when a certain sample to be measured was measured with preliminarily fixed standard peak positions of the respective elements and digitalizing the coincident degree of the peak-generating positions with the standard peak positions to judge by the digitalized value whether a certain element is contained in the sample to be measured.

Even in the case where the resolution is changed by the exchange of the detector element, the qualitative analysis can be accurately achieved by setting the coefficient in the digitalizing expression, depending upon the resolution of the detector.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A fluorescent X-ray qualitative analytical method comprising:
   preliminarily measuring a standard peak position corresponding to an energy position of fluorescent rays generated from each element expected in a sample;
   storing each standard peak position;
   radiating the sample with X-rays to cause fluorescent X-rays from the elements in the sample;
   obtaining spectral data from the fluorescent X-rays generated from a sample to determine a peak-generating position from the spectral data;
   comparing the peak-generating position obtained from the spectral data with said standard peak position by a spectral operation of separation of the peaks from the spectral data in accordance with an overlapped factor method; and
   determining that an element is contained in the sample, if the peak-generating position of the spectral data from the sample coincides with the standard peak position of an element.

2. A fluorescent X-ray qualitative analytical method comprising:
   preliminarily measuring a standard peak position corresponding to an energy position of fluorescent rays generated from each element expected in a sample;
   storing each standard peak position;
   radiating the sample with X-rays to cause fluorescent X-rays from the elements in the sample;
   obtaining spectral dam from the fluorescent X-rays generated from a sample to determine a peak-generating position from the spectral data;
   comparing the peak-generating position obtained from the spectral data with said standard peak position by a spectral operation of separation of the peaks from the spectral data in accordance with a method of least squares; and
   determining that an element is contained in the sample, if the peak-generating position of the spectral data from the sample coincides with the standard peak position of an element.

3. A fluorescent X-ray qualitative analytical method comprising the steps of:
   preliminarily measuring standard peak positions corresponding to energy positions of fluorescent rays generated from each element expected in a sample;
   storing each standard peak position;
   radiating the sample with X-rays to cause fluorescent X-rays from the elements in the sample;
   obtaining spectral data from the fluorescent X-rays generated from a sample to determine a peak-generating position from the spectral data;
   selecting an element having respective peak-generating positions from the plurality of peak-generating positions obtained from the spectral data;
   simultaneously selecting also elements having peak-generating positions existable in the vicinity of the respective peak-generating positions of said preliminarily selected element including the respective peak-generating positions for every peak-generating position;
   providing a weighting factor of the elements having peak-generating positions in the vicinity, depending on their proximate position to the stored standard peak positions to provide a weighted peak-generating position;
   comparing the weighted peak-generating position obtained from the spectral data with said standard peak position; and
   determining that an element is contained in the sample, if the weighted peak-generating position of the spectral data from the sample is within a predetermined value of the standard peak position of an element.

4. The invention of claim 3 wherein the comparing step is performed by the use of a method of least square or the overlapped factor method.

5. The invention of claim 3 further including repeating the above steps of selecting, simultaneously selecting, comparing, and determining for all elements to be qualitatively analyzed.

6. A fluorescent qualitative analytical method in which X-rays generated from an X-ray generator are incident upon a sample to be measured, the fluorescent X-rays emitted from the sample are detected by means of a detector, and signals are read as spectral data through a signal-operating means, comprising the steps of:
   obtaining spectral data from fluorescent X-rays emitted from a sample to be measured to determine peak-generating positions generated in said spectral data;
   comparing said peak-generating positions obtained from the spectral data with predetermined standard peak positions of the respective elements and digitizing the coincident degree of the peak-generating positions with said standard peak positions; and judging that an element is contained in the sample when an obtained value is equal to a predetermined value or greater and is not contained when the obtained value is less than the predetermined value, wherein the predetermined value for judging is made variable depending upon a sample system to be measured.

7. A fluorescent X-ray qualitative analytical method as set forth in claim 6, wherein said digitalization is conducted by the following expression (1):

$$y = \Sigma\{[(A \times h - \Delta E) \times I]/(A \times h)\}/\Sigma I \quad (1)$$

wherein when $A \times h - \Delta E < 0$ holds good, $A \times h - \Delta E$ is defined as 0,
- y: value for a certain element
- A: coefficient
- h: height of the peak measured
- $\Delta E$: shift between the peak-generating position (peak position measured) and the standard peak position (peak position generated from the certain element
- I: weight corresponding to the generating probability of the peak.

8. A fluorescent qualitative analytical method in which X-rays generated from an X-ray generator are incident upon a sample to be measured, the fluorescent X-rays emitted from the sample are detected by means of a detector, and signals are read as spectral data through a signal-operating means, comprising the steps of:
- obtaining spectral data from fluorescent X-rays emitted from a sample to be measured to determine peak-generating positions generated in said spectral data;
- comparing said peak-generating positions obtained from the spectral data with predetermined standard peak positions of the respective elements;
- digitizing the coincident degree of the peak-generating positions with said standard peak positions, wherein said digitalization is conducted by the following expression:

$$y = \Sigma\{[(A \times h - \Delta E) \times I]/(A \times h)\}/\Sigma I$$

wherein, when $A \times h - \Delta E < 0$ holds good, $A \times h - \Delta E$ is defined as 0,
- y: value for a certain element
- A: coefficient
- h: height of the peak measured
- $\Delta E$: shift between the peak-generating position (peak position measured) and the standard peak position (peak position generated from the certain element
- I: weight corresponding to the generating probability of the peak; and
- judging that an element is contained in the sample when an obtained value is equal to a predetermined value or greater and is not contained when the obtained value is less than the predetermined value.

9. A fluorescent X-ray qualitative analytical method as set forth in claim 8 wherein the predetermined value for judging is made variable for every element.

10. A fluorescent X-ray qualitative analytical method as set forth in claim 8 wherein the predetermined value for judging is made variable depending upon a sample system to be measured.

11. A fluorescent X-ray qualitative analytical method comprising:
- preliminarily measuring standard peak positions corresponding to energy positions of fluorescent rays generated from each element expected in a sample;
- consolidating adjacent peak positions, each representative of an element that are within a predetermined distance from each other as a single combined standard peak position for those elements;
- storing each standard peak position;
- radiating the sample with X-rays to cause fluorescent X-rays from the elements in the sample;
- obtaining spectral data from the fluorescent X-rays generated from a sample to determine peak-generating positions from the spectral data;
- comparing the peak-generating position obtained from the spectral data with said standard peak position; and
- determining that an element is contained in the sample, if the peak-generating position of the spectral data from the sample coincides with the standard peak position of an element.

12. The invention of claim 11 further including repeating the determining step for each element to be qualitatively analyzed.

13. A fluorescent X-ray qualitative analytical method as set forth in claim 11 wherein the coincident degree of the compared peak-generating positions with the standard peak positions are digitized, and wherein said digitalization is conducted by the following expression:

$$y = \Sigma\{[(A \times h - \Delta E) \times I]/(A \times h)\}/\Sigma I$$

wherein, when $A \times h - \Delta E < 0$ holds good, $A \times h - \Delta E$ is defined as 0,
- y: value for a certain element
- A: coefficient
- h: height of the peak measured
- $\Delta E$: shift between the peak-generating position (peak position measured) and the standard peak position (peak position generated from the certain element
- I: weight corresponding to the generating probability of the peak.

14. A fluorescent qualitative analytical method in which X-rays generated from an X-ray generator are incident upon a sample to be measured, the fluorescent X-rays emitted from the sample are detected by means of a detector, and signals are read as spectral data through a signal-operating means, comprising the steps of:
- obtaining spectral data from fluorescent X-rays emitted from a sample to be measured to determine peak-generating positions generated in said spectral data;
- comparing said peak-generating positions obtained from the spectral data with predetermined standard peak positions of the respective elements and digitizing the coincident degree of the peak-generating positions with said standard peak positions; and
- judging that an element is contained in the sample when an obtained value is equal to a predetermined value or greater and is not contained when the obtained value is less than the predetermined value, wherein the predetermined value for judging is made variable for every element.

15. A fluorescent X-ray qualitative analytical method as set forth in claim 14 wherein said comparing operation is conducted for all elements to be qualitatively analyzed.

* * * * *